United States Patent
Koodathingal et al.

(10) Patent No.: US 12,215,378 B2
(45) Date of Patent: Feb. 4, 2025

(54) RNA IDENTITY METHOD USING RNASE H DIGESTION AND SIZE FRACTIONATING

(71) Applicants: GLAXOSMITHKLINE BIOLOGICALS SA, Rixensart (BE); Prakash Koodathingal, Rockville, MD (US); Ying Zhang, Rockville, MD (US)

(72) Inventors: Prakash Koodathingal, Rockville, MD (US); Ying Zhang, Rockville, MD (US)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 67 days.

(21) Appl. No.: 16/637,935

(22) PCT Filed: Aug. 10, 2018

(86) PCT No.: PCT/IB2018/056038
§ 371 (c)(1),
(2) Date: Feb. 10, 2020

(87) PCT Pub. No.: WO2019/030718
PCT Pub. Date: Feb. 14, 2019

(65) Prior Publication Data
US 2020/0325527 A1    Oct. 15, 2020

Related U.S. Application Data

(60) Provisional application No. 62/544,096, filed on Aug. 11, 2017.

(51) Int. Cl.
*C12Q 1/6816* (2018.01)
*A61K 39/00* (2006.01)

(52) U.S. Cl.
CPC .......... *C12Q 1/6816* (2013.01); *A61K 39/00* (2013.01); *A61K 2039/53* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 6,040,138 A * | 3/2000 | Lockhart | C12Q 1/6837 536/24.31 |
| 6,544,741 B1 * | 4/2003 | Mugasimangalam | C12N 15/1096 435/91.51 |
| 2002/0142308 A1 | 10/2002 | Dattagupta et al. | |
| 2005/0164226 A1 * | 7/2005 | Huang | C12Q 1/6813 435/6.1 |

(Continued)

FOREIGN PATENT DOCUMENTS

| | | |
|---|---|---|
| WO | 9821359 A1 | 5/1998 |
| WO | 0245472 A2 | 6/2002 |
| WO | 2016180430 A1 | 11/2016 |

OTHER PUBLICATIONS

Goodrich TT, Lee HJ, Corn RM. Direct detection of genomic DNA by enzymatically amplified SPR imaging measurements of RNA microarrays. J Am Chem Soc. Apr. 7, 2004;126(13):4086-7. (Year: 2004).*

(Continued)

*Primary Examiner* — Michelle S Horning

(57) ABSTRACT

Methods, compositions, kits, and uses are provided herein for detecting a subject nucleic acid in various samples.

11 Claims, 5 Drawing Sheets

Figure 1:
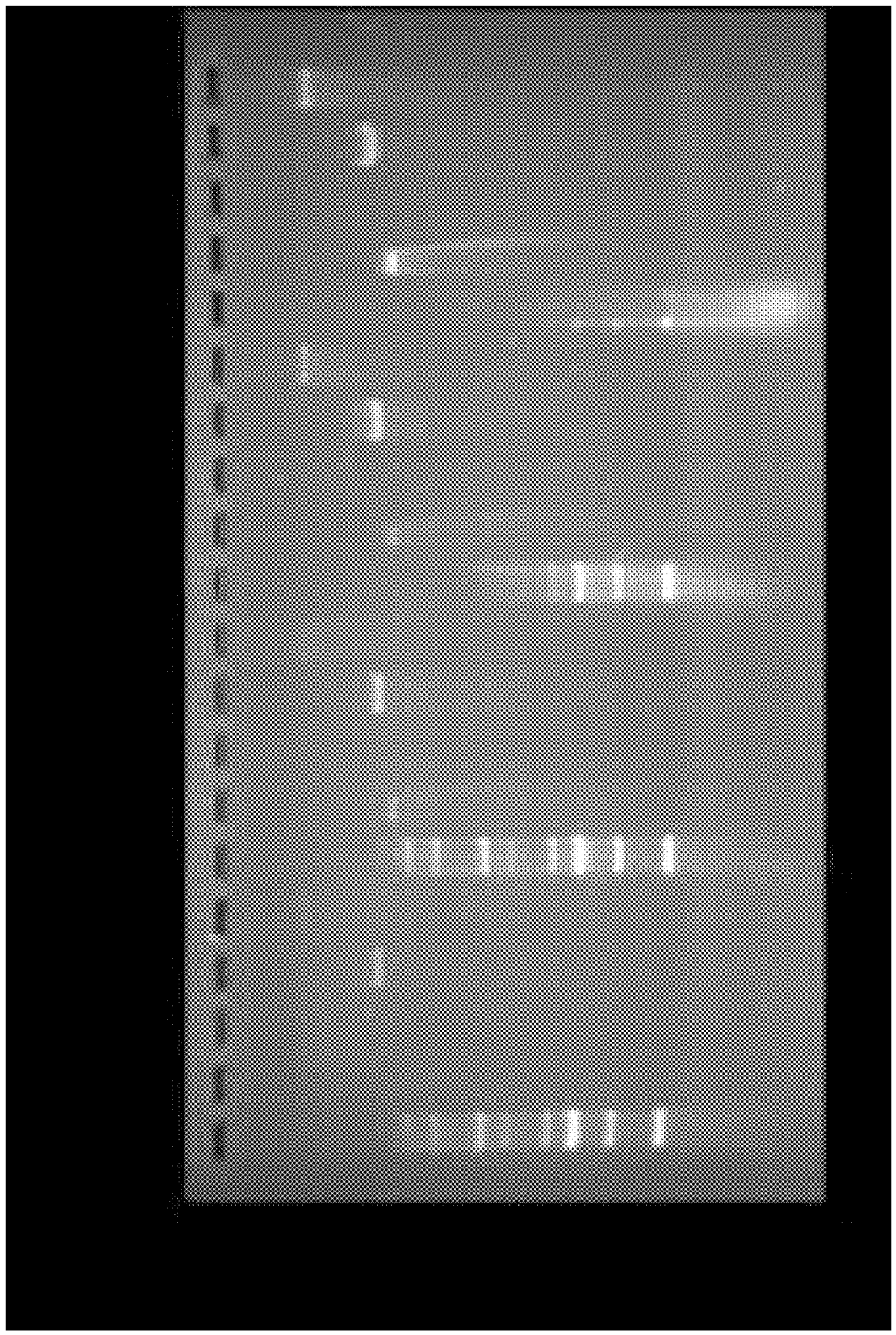

Specification includes a Sequence Listing.

(56) References Cited

U.S. PATENT DOCUMENTS

2008/0227653 A1* 9/2008 Fodor .................. C12Q 1/6809
506/9

OTHER PUBLICATIONS

Bryant S, Manning DL. Formaldehyde gel electrophoresis of total RNA. Methods Mol Biol. Humana Press. 1998;86:69-72. (Year: 1998).*

International Search Report and Written Opinion for corresponding International Application No. PCT/IB2018/056038, mailed Oct. 1, 2018 (11 pages).

Duncan et al., "Structural analysis of templates and RNA polymerase III transcripts of Alu family sequences interspersed among the human β-like globin genes", Gene, vol. 13, Issue 2, 1981, p. 185-196.

* cited by examiner

RNA IDENTITY METHOD USING RNASE H DIGESTION AND SIZE FRACTIONATING

CROSS-REFERENCE TO RELATED APPLICATIONS

This application is filed pursuant to 35 U.S.C. § 371 as a United States National Phase Application of International Patent Application Serial No. PCT/IB2018/056038 filed Aug. 10, 2018, which claims priority to U.S. Provisional Application No. 62/544,096 filed Aug. 11, 2017, the complete contents of each of which are hereby incorporated by reference for all purposes.

FIELD OF THE INVENTION

The present invention provides methods and compositions for detecting a nucleic acid having a specific sequence in various samples.

BACKGROUND TO THE INVENTION

Detecting RNA having a specific sequence is useful in life science research, manufacturing, and clinical fields. For instance, the presence or absence of an RNA of interest in a tissue sample taken from a subject can provide information related to gene expression of diseased versus normal, treated versus untreated, gene upregulated versus gene downregulated status of the subject. Or, confirming the presence and amount of RNA within a manufactured biological product may be used to provide information regarding contaminating organisms in the product. In addition, confirming the presence and amount of RNA may be needed to satisfy regulations requiring testing a manufactured RNA product to confirm the product is RNA, free of process impurities such as template DNA, and is correctly identified prior to sale or shipping. And the presence of pathogenic RNAs in a clinical sample can provide information regarding the type and amount of an infective agent, thereby allowing the prediction of disease progression and therapeutic efficacy.

Methods for determining the presence and/or quantity of a target RNA in a sample include, for example, Northern blot, RT-PCR, invasive cleavage assay, and the like. The most suitable assay may vary from application to application. One advantage of assays like Northern blot and invasive cleavage assay is that there is no need for target amplification.

In one example of a cleavage assay called the "invasive cleavage assay," there is a primary reaction in which one-nucleotide overlap substrates are generated by the hybridization of invasive deoxy oligonucleotides and probe deoxy oligonucleotides to their respective RNA targets. Each probe contains a specific, target-complementary region and a generic noncomplementary 5'-flap, which is released through 5'-nuclease cleavage. In the presence of a 5'-nuclease, multiple probes are cleaved per invasive oligonucleotide, resulting in target specific accumulation of 5'-flap. After completion of the primary reaction, the cleaved 5'-flaps then act as invasive oligonucleotides in a secondary reaction in which they stably bind to the appropriate secondary-reaction template. FRET deoxy oligonucleotides that form an overlap structure with the 5'-flap-secondary-reaction template are then cleaved by the 5' nuclease. Fluorescence signal is generated when multiple FRET deoxy oligonucleotides are cleaved per 5'-flap-secondary-reaction template complex and is detected. In another example of a cleavage assay, a RNA product is incubated with various nucleotide probes complementary to the RNA product under conditions that allow the formation of duplexes, followed by digestion with an RNase (such as RNase H or RNase TI) to form reaction products. See WO2016/180430. The reaction products are subject to chromatography and the sequence determined to confirm the identity of the products.

Notwithstanding the present availability of assays, there remains a need for reproducible and specific methods for the detection of RNA having a particular sequence in various samples.

SUMMARY OF THE INVENTION

Methods, compositions, kits, and uses are provided herein for detecting a subject nucleic acid in various samples.

In some aspects, a method is provided for detecting a subject nucleic acid, comprising the steps of contacting a sample suspected of containing the subject nucleic acid with a query nucleic acid complementary to a portion of the subject nucleic acid under conditions that the query nucleic acid specifically hybridizes with the subject nucleic acid, when present, to form a hybrid duplex, wherein the query and subject nucleic acids have different five-carbon sugars; adding a nuclease specific to hybrid duplexes to the sample under conditions that facilitate specific cleavage of the subject nucleic acid when the hybrid duplex is present; and size fractionating the sample and determining the presence of cleaved subject nucleic acid, wherein the presence of two or more cleavage products of the subject nucleic acid of predicted size confirms the presence of the subject nucleic acid in the sample. In some aspects, the subject nucleic acid is an RNA. In some aspects, the query nucleic acid is DNA. In some aspects, the nuclease specific to hybrid duplexes is an RNAse H. In some aspects, the method may be used for confirming the absence of a subject nucleic acid.

In some aspects, a method is provided for detecting a subject RNA, comprising the steps of contacting the sample with a query DNA oligonucleotide complementary to a portion of the subject RNA under conditions that the query DNA oligonucleotide specifically hybridizes with the subject RNA, when present, to form a hybrid duplex; adding RNAse H to the sample under conditions that facilitate specific cleavage of the subject RNA when the hybrid duplex is present; and size fractionating the sample and determining the presence of cleaved subject RNA, wherein the presence of cleavage products of the subject RNA confirms the presence of the subject RNA in the sample.

In some aspects, a kit is provided comprising a query DNA oligonucleotide complementary to a portion of a subject RNA; an RNase H; and a reaction medium suitable for use under conditions in which the query DNA oligonucleotide specifically hybridizes with the subject RNA, when present, to form a hybrid duplex and to facilitate specific cleavage of the subject RNA when the hybrid duplex is present. In some aspects, the kit includes a control RNA and a query DNA oligonucleotide complementary to a portion of a control RNA.

In some aspects is provided a use of the method or the kit of any of the preceding aspects for confirming the identity of a subject RNA produced by a process for manufacturing the subject RNA.

DESCRIPTION OF DRAWINGS/FIGURES

FIG. 1. Denaturing agarose gel electrophoresis highlighting RNAse A mediated degradation of SAM RNA but not DNA. Samples correspond to table 1, and Experimental set up is as in section 3.2.

Figure 2:
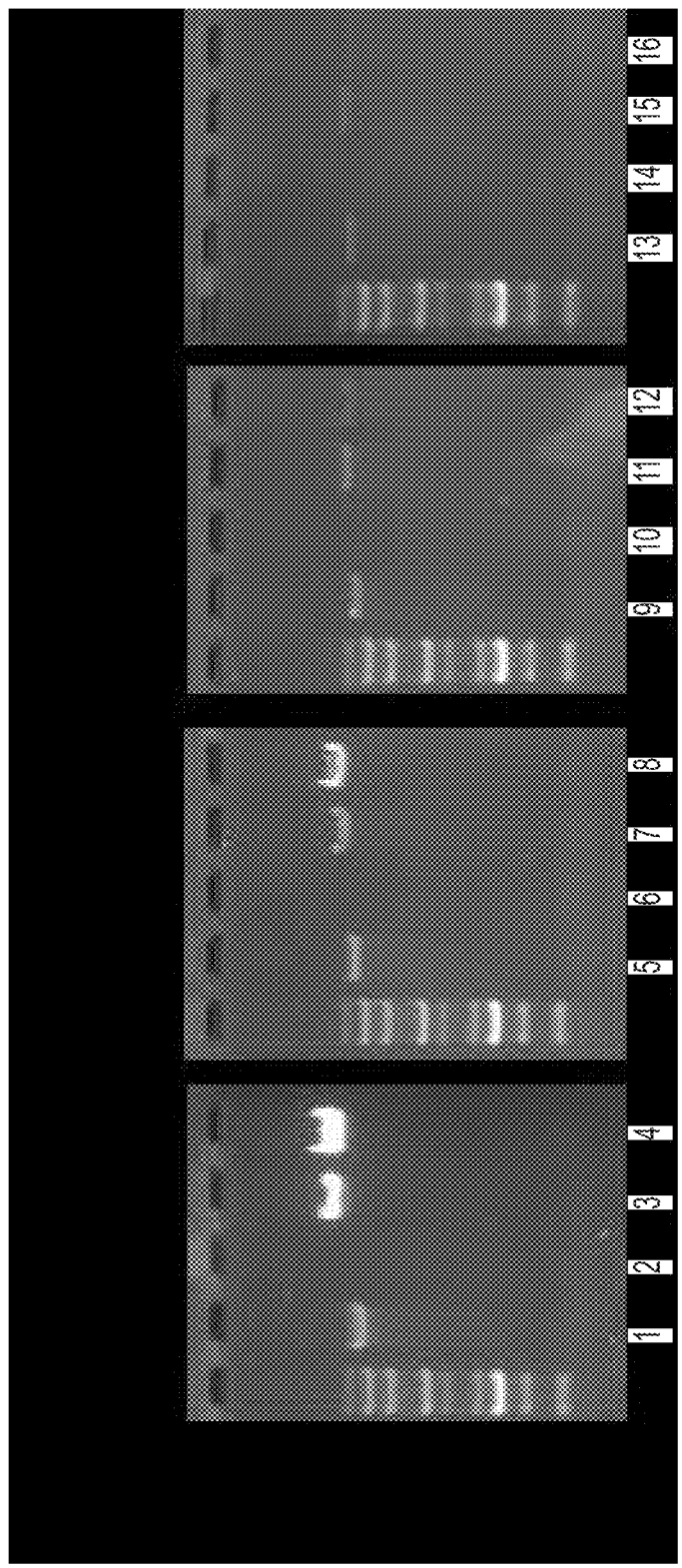

FIG. 2. Denaturing agarose gel electrophoresis highlighting RNAse T1 mediated degradation of SAM RNA but not DNA. Samples correspond to table 2.

Figure 3:
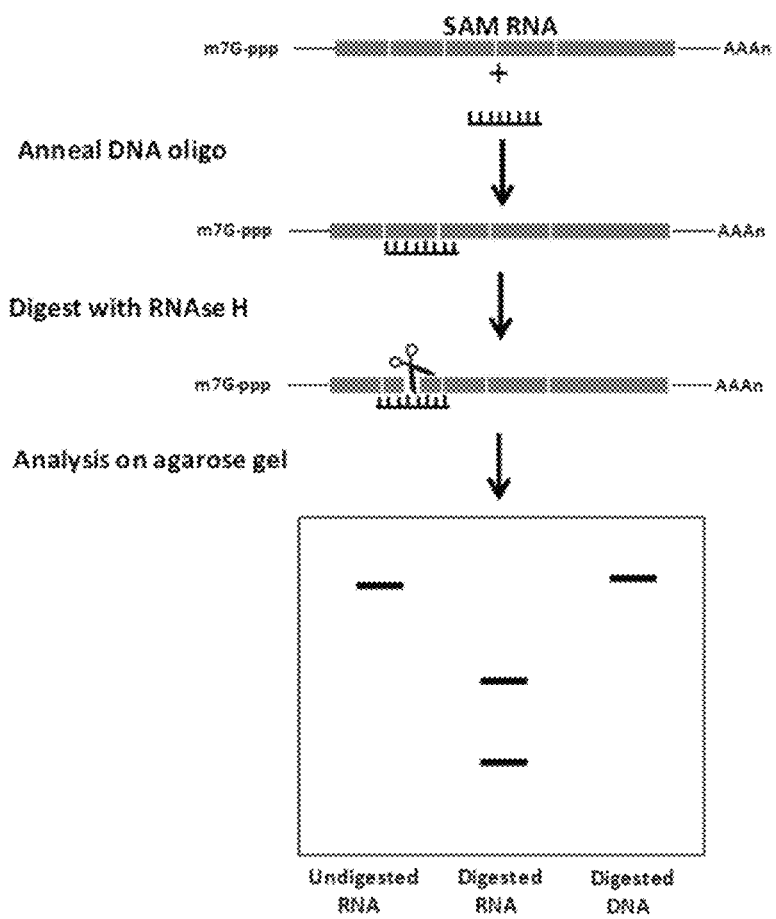

FIG. 3. Schematic of an RNA identity assay utilizing RNAse H capable of distinguishing SAM RNA from contaminating DNA or other non-specific RNAs.

Figure 4:
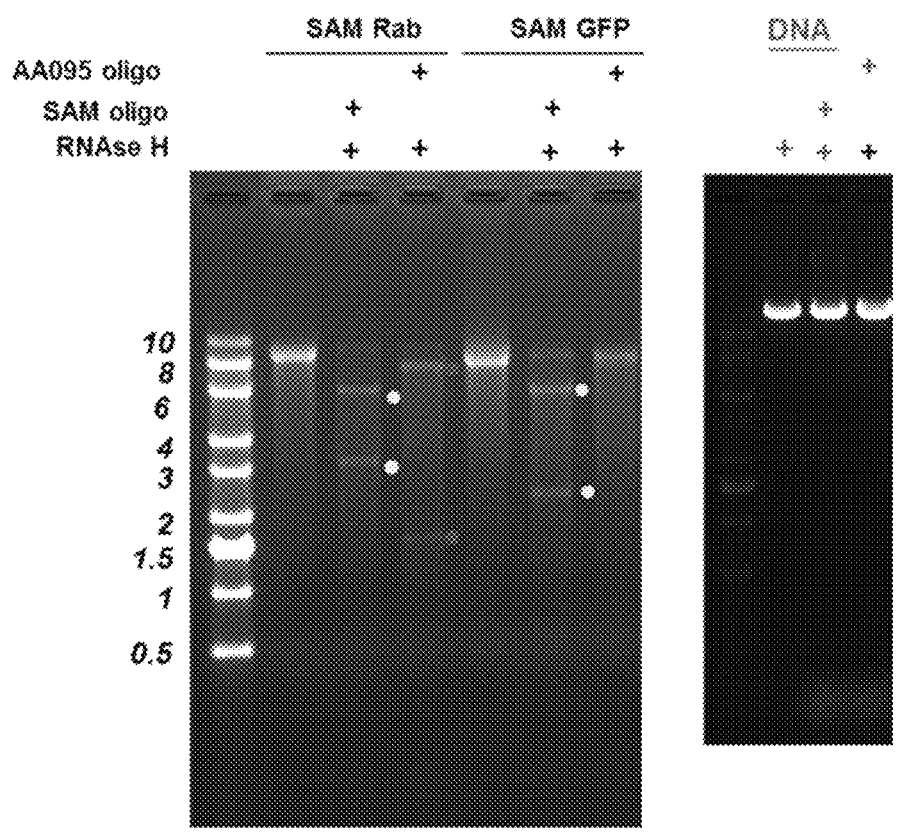

FIG. 4. Denaturing agarose gel electrophoresis highlighting the capability of the identity assay to distinguish between two different RNA sequences. Each lane represents sample treatments as described in the figure. SAM Rab represents RNA containing sequence coding for a rabies antigen. SAM GFP represents RNA containing sequence coding for GFP (Green Fluorescent Protein). The AA095 oligo is specific to the SAM Rabies RNA and produces fragments of only it. The SAM oligo binds both the SAM Rabies and SAM GFP RNA and produces fragments. Both oligos do not produce fragments with DNA and serve as the negative specificity control.

Figure 5:
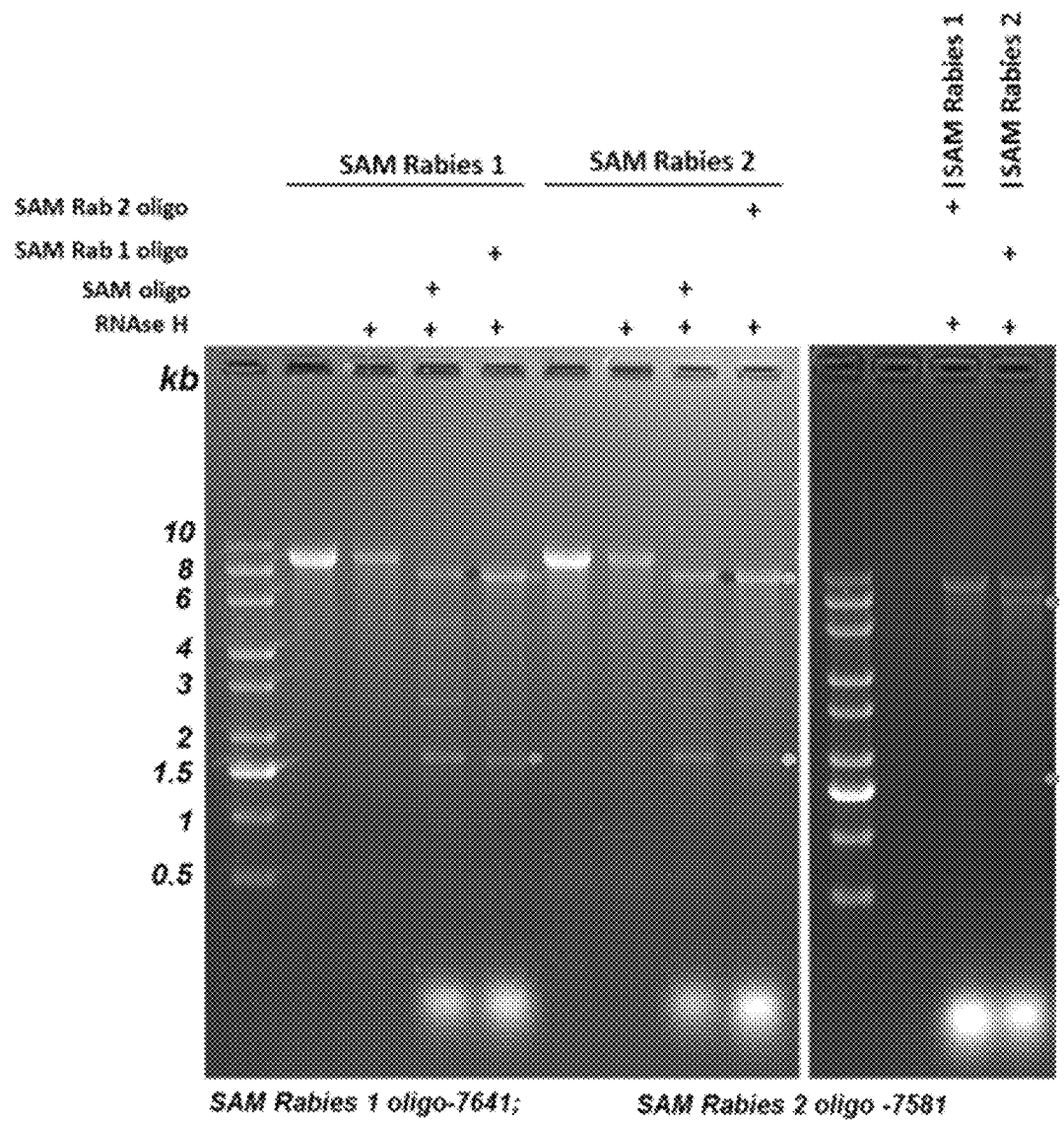

FIG. 5. Denaturing agarose gel electrophoresis highlighting the capability of the identity assay to distinguish between two closely related RNAs (SAM Rabies 1 and SAM Rabies 2) with more than 80% sequence identity. Each lane represents sample treatments as described in the figure. SAM oligo binds both RNAs and produce fragments. However, SAM Rab 1 oligo and SAM Rabies 2 oligo are specific to SAM Rabies 1 & 2 respectively, and produce fragments with reduced efficiency when used non-specifically (see last 2 lanes of the $2^{nd}$ gel).

DETAILED DESCRIPTION OF THE INVENTION

Definitions

By the term "subject nucleic acid" is intended a polynucleotide whose presence is to be determined or identity is to be confirmed in a sample. In some aspects, alternatively, the absence of a polynucleotide in a sample is to be confirmed. A subject nucleic acid includes a "subject RNA," by which is intended a RNA whose presence is to be determined or identity is to be confirmed in a sample. In certain aspects, the subject nucleic acid encodes a polypeptide sequence. For instance, a subject nucleic acid may be a RNA vector that encodes a polypeptide. The polypeptide may be an immunogen such as an antigen, e.g., that, when administered in an effective amount to a mammal, optionally with an adjuvant, raises an immune response to a bacteria, virus, fungus, or protozoan. In some aspects, such a vector may be a self-replicating RNA. In some aspects, a subject nucleic acid may be a RNA vaccine comprising vector and insert sequence that together comprise a self-replicating RNA encoding an immunogen, such as an antigen for inducing an immunogenic response in a subject.

By the term "query nucleic acid" is intended a polynucleotide shorter than the subject nucleic acid. A query nucleic acid includes a query DNA, such as a DNA oligonucleotide. The length of the query nucleic acid is such that, for example, for the given complexity of a sample, the query nucleic acid can specifically hybridize with the subject nucleic acid so as to properly identify or detect it. A query nucleic acid is substantially complementary to a portion of the subject nucleic acid, such that the two will hybridize through canonical Watson-Crick style base pairing under suitable conditions including, in certain aspects, low, moderate, or stringent hybridization conditions.

By the term "distinct query nucleic acid" is intended a query nucleic acid having a specific nucleotide sequence. While it is conceivable that the present methods could be carried out using a single molecule of a distinct query nucleic acid, typically a distinct query nucleic acid is present in the methods herein as a plurality of molecules, each having the same sequence. In some aspects, the number of molecules of distinct query nucleic acid utilized will be determined by the number of subject nucleic acid molecules suspected to be present in the samples, i.e., a specific ratio of query nucleic acid molecules to subject nucleic acid molecules will be utilized, as described elsewhere herein. Where more than one distinct query nucleic acid is utilized in the present method, each distinct query nucleic acid is typically present as a population of molecules having a distinct nucleotide sequence.

By "five carbon sugar" is intended a pentose monosaccharide, including both ribose and deoxyribose.

By "a nuclease specific to hybrid duplexes" is intended a nuclease that catalyzes the hydrolysis of a polynucleotide substantially only in the presence of a hybrid nucleic acid duplex, such as DNA/RNA. Exemplary nucleases specific to hybrid duplexes include, for example RNAse H (RNAse H1, H2 and H3, described in Tadokoro et al. (2009) *FEBS Journal*, 276:1482-1493. Nuclease specific to hybrid duplexes need not cut the duplex per se, that is, the cleavage may be, but need not be, in the region of the duplex, e.g., the subject nucleic acid could be cleaved outside of the hybrid duplex region. If the cleavage is in the hybrid duplex region, either strand (i.e., subject or query) could be cleaved, including, in some aspects, both. In short, the nuclease simply leads to a detectable cleavage event, e.g., of the subject nucleic acid, but only when the query nucleic acid is present.

Methods

Nucleic Acid Samples

Methods are provided for detecting a subject nucleic acid in a sample. In some aspects, the sample that may comprise a subject nucleic acid is a liquid sample comprising a liquid suitable for use with RNA, including for instance an aqueous liquid. In some aspects, the nucleic acid is solubilized in the liquid. In some aspects, the liquid is a buffer comprising excipients. In some aspects, the sample is a portion of a completed transcription reaction in which DNA was transcribed into RNA. In some aspects, the sample is purified prior to use in the present method to, among other things, remove template DNA. RNA transcription reactions, methods, and buffers suitable for the purification of RNA are described in WO/2014/140211. In some aspects the sample is a vaccine product for which the identity must be confirmed.

In some aspects, a subject nucleic acid is RNA. In some aspects, a query nucleic acid is DNA. In such aspects, the methods herein are useful to detect the presence of contaminating template DNA, because RNase will not cleave any template DNA present in the sample. Thus, contaminating DNA template present in the sample will remain uncleaved in the method (because RNase H will not cleave a DNA: DNA duplex) and can be detected as an uncleaved product. See FIG. 3.

In some aspects, the subject nucleic acid encodes a polypeptide of interest. In some aspects, the polypeptide of interest is an antigen that, when administered in an effective amount to a mammal, optionally with an adjuvant, raises an immune response to a bacteria, virus, fungus, or protozoan. In some aspects, the subject nucleic acid is a self-replicating RNA.

In some aspects of the method described elsewhere herein, more than one, two, or three different subject nucleic acids are suspected to be present. In some aspects, a plurality of different nucleic acids are present. In such aspects, each different subject nucleic acid differs from each of the other subject nucleic acids by at least one nucleotide. In other words, each different subject nucleic acid has a "unique portion" that differs from the other different subject nucleic acids by at least one nucleotide. In particular, one subject nucleic acid differs from another subject nucleic acid by at least 1, 2, 3, 4, 5, 6, 7, 8, 9, 10, 11, 12, 13, 14, 15, or more nucleotides. In another aspect, one subject nucleic acid has at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% sequence identity to a different subject nucleic acid. Thus, by use of distinct query nucleic acids, each complementarity to a portion of a subject nucleic acid that differs from the other subject nucleic acid, one may utilize the methods herein to detect and/or identify more than one subject nucleic acid in a sample by the presence of cleavage products of a size predicted for that subject nucleic acid.

Query Nucleic Acids and Hybridization Conditions

Where the nucleotide sequence and overall length of the subject nucleic acid is known, the query nucleic acid may be designed to hybridize to a specific portion of the subject nucleic acid and the size of resulting cleavage products can be predicted. In aspects where more than one query nucleic acid may be present, the query nucleic acids are designed to bind to a portion of a subject nucleic acid at which the sequence of the subject nucleic acid differs from the other subject nucleic acid and which will produce cleavage products from a subject nucleic acid that are of a different size from the cleavage products produced from the other subject nucleic acid(s). In this way, size fractionation may be utilized to detect or identify the presence (or absence) of a subject nucleic acid complementary to the query nucleic acid.

In some aspects, the subject nucleic acid comprises a vector nucleotide sequence and at least one distinct query nucleic acid comprises a nucleotide sequence complimentary to a portion of the vector nucleotide sequence. In some aspects, the subject nucleic acid is RNA and the vector nucleotide sequence comprises the necessary control elements and encodes the necessary non-structural protein products such that the RNA is a self-replicating RNA. In these aspects, if the method results in a cleavage product, the method can be used to distinguish between a subject nucleic acid that is RNA and a contaminating RNA that has a different sequence (the contaminating RNA will not hybridize to form a duplex with the query nucleic acid and will not produce a cleavage product) or between a subject nucleic acid that is RNA and contaminating template DNA (the contaminating DNA will not be cleaved by RNase H and will not produce a cleavage product).

In some aspects, the subject nucleic acid comprises a particular insert nucleotide sequence and at least one distinct query nucleic acid is complimentary to a portion of the insert sequence. The insert sequence may encode a polypeptide of interest. In these aspects, if the method results in a cleavage product, the method can be used to distinguish between a subject nucleic acid that is RNA and comprises the particular insert sequence and a contaminating RNA that has a different insert or no insert nucleotide sequence (the subject nucleic acid will hybridize to the query nucleic acid and produce a cleavage product; a contaminating RNA will not hybridize with the query nucleic acid specific for the insert and will not produce a cleavage product). Such methods can be used to confirm the identity of a subject RNA by insert nucleotide sequence, for instance, when manufacturing a RNA in a facility that makes multiple different products that each have the same vector, but that differ by their insert nucleotide sequence.

In some aspects, the method comprises contacting the sample with two or more distinct query nucleic acids, each distinct query nucleic acid complementary to a different portion of the subject nucleic acid. In these aspects, more than two cleavage products will result, depending on the number of query nucleic acids utilized.

In some aspects, the subject nucleic acid comprises both vector and insert nucleotide sequence and the method further comprises contacting the sample with two or more distinct query nucleic acids, wherein at least one of the two or more distinct query nucleic acids is complementary to a portion of the vector nucleotide sequence and at least one of the two or more distinct query nucleic acids is complementary to a portion of the insert nucleotide sequence. In these aspects, the presence of uncleaved product indicates the presence of contaminating RNA that lacks both the expected vector and the insert nucleotide sequence, or the presence of contaminating template DNA. The presence of some cleavage products, but fewer than expected, indicates the presence of RNA that lacks either the expected vector nucleotide sequence or the expected insert nucleotide sequence. The size of the products can be compared to the expected size predicted for products resulting from cleavage at the vector sequence or from cleavage at the insert sequence to determine whether it is vector or insert nucleotide sequence that is different than expected. In these aspects, one is able to confirm the identity of a subject nucleic acid by size fractionation, without resort to complicated chromatography, analytical, and sequencing techniques.

One may wish to analyse a sample that may contain two or more subject nucleic acid sequences. For instance, the sample may be expected to contain a combination vaccine wherein two or more RNA vaccines are present, a first RNA vaccine encoding a first polypeptide antigen and a second RNA vaccine encoding a second polypeptide antigen. In some aspects, a sample may be suspected to contain more than one subject nucleic acid, i.e., it may contain two or more populations of nucleic acids, each population having a nucleotide sequence distinct from every other population.

Accordingly, in some aspects the method further detects the presence of a second subject nucleic acid and a sample may comprise the second subject nucleic acid. The second subject nucleic acid differs from the first subject nucleic acid by at least one nucleotide. The method of this aspect includes a step of contacting the sample with at least one distinct query nucleic acid complementary to a portion of the second subject nucleic acid that differs by at least one nucleotide from the first subject nucleic acid, wherein said second subject nucleic acid is RNA and the distinct query nucleic acid is DNA. This aspect further includes a step of determining the presence of cleaved second subject nucleic acid, wherein the presence of two or more cleavage products of the second subject nucleic acid of predicted size confirms the presence of the second subject nucleic acid in the sample.

In some aspects the method further detects the presence of a third subject nucleic acid and a sample may comprise the third subject nucleic acid. The third subject nucleic acid differs from the first and second subject nucleic acids by at least one nucleotide. The method of this aspect includes a step of contacting the sample with at least one distinct query nucleic acid complementary to a portion of the third subject nucleic acid that differs by at least one nucleotide from the first and second subject nucleic acids, wherein said third subject nucleic acid is RNA and the distinct query nucleic acid is DNA. This aspect further includes a step of determining the presence of cleaved third subject nucleic acid, wherein the presence of two or more cleavage products of the third subject nucleic acid of predicted size confirms the presence of the third subject nucleic acid in the sample.

In some aspects the method further detects the presence of a plurality of different subject nucleic acids, wherein the sample may comprise a plurality of different subject nucleic acids, each subject nucleic acid differing from the other subject nucleic acid by at least one nucleotide, wherein the sample is contacted with a plurality of distinct query nucleic acids, each distinct query nucleic acid complementary to a unique portion of one individual subject nucleic acid out of the plurality of different subject nucleic acids, wherein said plurality of subject nucleic acids are RNA and the distinct query nucleic acids are DNA, and then determining the presence of cleaved products of each of the subject nucleic acids, wherein the presence of two or more cleavage products of one individual subject nucleic acid out of the plurality of different subject nucleic acids of predicted size confirms the presence of the one individual subject nucleic acid out of the plurality of different subject nucleic acids in the sample.

The sequence of a distinct query nucleic acid and the conditions under which it hybridizes to the subject nucleic acid may be adjusted for use within the present methods. In some aspects, a query nucleic acid is designed to hybridize to the subject nucleic acid at low, moderate, or stringent hybridization conditions.

In some aspects, a query nucleic acid is a DNA oligonucleotide. In some aspects, an oligonucleotide is 12 or more nucleic acids in length. In some aspects, an oligonucleotide is between 12 and 40 nucleotides, inclusive. In some aspects, an oligonucleotide is 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. In some aspects, an oligonucleotide is between 15 and 25 nucleotides, inclusive.

In some aspects, each distinct query nucleic acid comprises between 40-60%, 45-55%, 46-54%, 47-53%, 48-52%, 49-51% G-C content, inclusive. In some aspects, each distinct query nucleic acid comprises about 50 G-C content.

In some aspects the query nucleic acid is 80, 85, 86, 87, 88, 89, 90, 91, 92, 93, 94, 95, 96, 97, 98, 99%, or more, e.g., 100% identical to the complement of the subject nucleic acid over the entire length of the query nucleic acid, e.g., for a query nucleic acid having a complementary portion of 20 nucleotides, fewer than 4, 3, 2, or 1 nucleotides mismatch with the complementary portion of the subject nucleic acid. Of course, in some aspects, the query nucleic acid may include additional functional sequences, such as adapter sequences, that may have substantially no complementarity to the subject nucleic acid and the lengths, complementarity, etc. referred to herein means the portion of the query nucleic acid adapted to hybridize to the subject nucleic acid, e.g., the "binding region" of the query nucleic acid. The query nucleic acid is complementary to a known portion of the subject nucleic acid, cf., random primers such as random hexamers. Methods for the design of query nucleic acids suitable to hybridize to a subject nucleic acid under various stringency are known in the art, including, for instance, on the world wide web at bioinformatics.nl/cgi-bin/primer3plus/primer3plus.cgi/ and idtdna.com/Primerquest/Home/Index.

In some aspects, the hybridization step of the methods are carried out in a media suitable for a query nucleic acid to specifically hybridize a subject nucleic acid that may be present in the sample. In some aspects, media suitable for hybridization are a liquid. In some aspects, solid media for hybridization may be utilized, for instance one or more distinct query nucleic acid(s) may be covalently or otherwise physically linked to a solid substrate. In some aspects, a liquid media is aqueous. In some aspects, an aqueous media is a buffer comprising excipients. In some aspects, a buffer is a citrate buffer. In some aspects, a citrate buffer comprises sodium citrate 10 mM, pH 6.2, 20 mM sodium chloride, 400 mM sucrose.

In some aspects, suitable conditions for a query nucleic acid to specifically hybridize with the subject nucleic acid are low, moderate, or stringent hybridization conditions, which conditions may be achieved by varying several parameters, including temperature. See, e.g., "Current Protocols in Molecular Biology" (Ausubel et al., eds.). In some aspects, the formation of the hybrid duplex is carried out at a temperature between 0-60° C.; 0-50° C.; 0-40° C.; 0-30° C.; 0-25° C.; 0-20° C.; 0-15° C.; 0-10° C.; or 2-6° C., inclusive. In some aspects, the formation of the hybrid duplex is carried out at a temperature of about 4° C.

Reaction Conditions

The conditions utilized during the cleavage reaction may be varied within the methods herein. For instance, in some aspects the specific cleavage of the subject nucleic acid is carried out at a temperature of between 0-50° C.; 25-45° C.; or 35-40° C., inclusive. In some aspects, the specific cleavage of the subject nucleic acid is carried out at a temperature of about 37° C.

The reaction conditions herein may also include further steps, including steps to finish the cleavage reaction. In some aspects, the specific cleavage of the subject nucleic acid the sample is subjected to a denaturing step. The denaturing step may be accomplished by adjusting the temperature, for instance in some aspects, the denaturing step comprises incubation at a temperature between 50-60° C., inclusive. In some aspects, the denaturing step comprises incubation at a temperature of 55° C. In some aspects, the incubation is carried out for a period of time between 1-60 minutes.

Analysis

The methods herein allow for the analysis of reaction products by methods such as size fractionation, although it is conceivable that one could further analyse the reaction products by methods as involved as sequencing, mass spectrometry, nuclear magnetic resonance, magnetic bead-probe sorting, and the like. By use of the methods herein, one is able to confirm the identity of a subject nucleic acid by size fractionation, without resort to complicated chromatography, analytical, and sequencing techniques.

Specifically, the presence of a cleavage product from RNase H digestion indicates that a duplex was formed between the query nucleic acid DNA and an RNA in the sample having the complementary sequence to the query nucleic acid. Given that single or double stranded DNA are not cleaved by RNAse H, this is a reliable method to distinguish RNA from the template DNA used for synthesizing RNA. Additionally, given that DNA oligos can be designed specifically to target RNAs with inserts of different antigenic regions, this method allows distinguishing different RNA vectors having different RNA inserts.

In some aspects, the size fractionating of the reaction products is by electrophoresis, such as agarose gel electrophoresis, capillary electrophoresis, electrophoresis on a microfluidic chip, or polyacrylamide gel electrophoresis. In some aspects, the agarose gel electrophoresis is denaturing agarose gel electrophoresis. Protocols for agarose gel electrophoresis for RNA may be found in "Current Protocols in Molecular Biology", Section 4.9 (Ausubel et al., eds.), or the reagents may be purchased as a kit (for instance Ambion's NorthernMax™ reagents for Northern Blotting, available from ThermoFisher Scientific on the world wide web at .thermofisher.com/us/en/home/references/protocols/ nucleic-acid-purification-and-analysis/rna-protocol/agarose-gel-electrophoresis-of-rna.html.

In some aspects, the reaction products are not subject to a sequencing reaction.

Kits, Uses

In some aspects, there is provided a kit for detecting a subject RNA, comprising one or more query DNA oligonucleotides complementary to a portion of the subject RNA; an RNase H; and a reaction medium suitable for use under conditions in which the query DNA oligonucleotide specifically hybridizes with the subject RNA, when present, to form a hybrid duplex and to facilitate specific cleavage of the subject RNA when the hybrid duplex is present. In some aspects, there is provided a use of the method or the kit as described herein for confirming the identity of a subject RNA produced by a process for manufacturing the subject RNA.

In some aspects, when using the methods or kits herein, the sample may be adjusted to achieve a particular concentration of nucleic acid, so long as the amount of nucleic acid is sufficient to be detected in the size fractionation step. In some aspects, the methods herein utilize samples diluted or concentrated to contain between 1 ng/μL and 1 μg/μL; 50 ng/μL and 900 ng/μL; 100 ng/μL and 800 ng/μL; 150 ng/μL and 700 ng/μL; 200 ng/μL and 600 ng/μL; 250 ng/μL and 500 ng/μL; or about 300 ng/μL of nucleic acid. In some aspects, the methods or kits herein utilize query nucleic acid at a particular molar ratio to the amount of nucleic acid in the sample. In some aspects, the query nucleic acid is utilized at 0.5-1.5 μg/μL; 0.6-1.4 μg/μL; 0.7-1.3 μg/μL; 0.8-1.2 μg/μL; 0.9-1.1 μg/μL; or about 1 μg/μL of query nucleic acid.

General

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount±10%.

The invention will be further described by reference to the following, non-limiting, figures and examples.

EXAMPLES

Example 1—Product Identity Assay Development; Abbreviations; Materials and Methods Various enzymes were considered in the development of a reproducible and specific assay able to determine the identity of an RNA in a sample. The objective of an RNA identity assay is to determine the identity of RNA in samples. It must distinguish the subject RNA from DNA, and from other potential contaminating RNA molecules as well.

In these experiments, drug substance and drug product samples containing SAM RNA were utilized. Overall, SAM RNA is approximately 9.5 kilo base (kb) in length, encompassing a 7.5 kb constant region encoding the proteins required for its own in vivo amplification and a 2 kb variable region encoding a vaccine antigen. The fully functional SAM RNA is synthesised by in vitro transcription of a plasmid template encoding the full length SAM RNA followed by enzymatic addition of a 7-methyl guanosine cap at the 5' end of the RNA. Subsequently, the template DNA is degraded utilizing a DNAse, and the SAM RNA is purified in a series of steps involving chromatography and filtrations to eliminate proteins and free nucleotides. In the drug substance, the SAM RNA is formulated in citrate buffer (Sodium citrate 10 mM, pH 6.2, 20 mM sodium chloride, 400 mM sucrose). In the clinic, before administration, SAM RNA is mixed with CNE, which serves as a synthetic delivery agent to facilitate entry of the SAM RNA into cells.

The feasibility of utilizing generic ribonucleases, RNAse A and RNAse T1, to determine the identity of SAM RNA was evaluated, as well as the feasibility of a more specific ribonuclease, RNAse H. Given that RNAse H does not degrade RNA in the absence of a complementary DNA oligonucleotide, RNAse H offered an approach that would avoid work place contamination. Studies were carried out to investigate RNase H accuracy in determining the identity of SAM RNA, as well as to investigate RNase H ability to discriminate SAM RNA from other contaminating RNAs or DNA.

Abbreviations

AD. analytical development
g. grams
L.O.D. limit of detection
LOQ. limit of quantitation
MOPS. 3-(N-morpholino) propanesulfonic acid
PG. pictogram
RNA. ribonucleic acid
SAM self-amplifying messenger
TD. technical development
μg. microgram
μl. microliter Materials RNA samples, including drug substance and drug product, produced in-house
DNA oligo, custom made commercially
RNAse A, (10 mg, >1000 U/mg), ThermoFisher Scientific P/N EN0531
RNAse T1, (1 U/μL) ThermoFisher Scientific P/N AM2283
RNAse H (5 U/μL), New England Biolabs P/N M0297S Methods Assay Conditions.

Samples containing 1 μg (or 3 μg or otherwise noted) of SAM RNA are first incubated on ice for 30 minutes in the presence of a complementary DNA oligo, followed by incubation for another 30 minutes in the presence of 2.5 U (or U/μL) of RNAse H at 37° C. The reaction was stopped by adding a stop buffer (such as denaturing agarose gel loading buffer), followed by incubation at 55° C. for 30 minutes, and separation of the RNAse H generated RNA fragments on a 1% denaturing agarose gel. The fragment sizes are determined in comparison to the RNA size marker. From the size distribution of the RNA fragments, the identity of SAM RNA is determined. For RNAse A and RNAse T1 reactions, the set up was as in Table 1 and 2, and the incubation, sample treatment and gel electrophoresis were as described above.

Example 2—Feasibility of an RNA Identity Assay Using Generic Ribonuclease RNAse A RNase A is an endoribonuclease that degrades single-stranded RNA at C and U residues. The feasibility of an RNA identity assay that distinguishes SAM RNA from DNA was studied using the approach set forth in Table 1 (experimental set up) with the results shown in FIG. 1.

TABLE 1

Experimental set up for the RNAse A mediated assay.

| | Ladder | RNA 1 | DNA 2 | RNA 3 | DNA 4 | RNA 5 | DNA 6 | RNA 7 | DNA 8 | RNA 9 | DNA 10 | RNA 11 | DNA 12 | RNA 13 | DNA 14 | RNA 15 | DNA 16 |
|---|---|---|---|---|---|---|---|---|---|---|---|---|---|---|---|---|---|
| Ladder | 4 ul | | | | | | | | | | | | | | | | |
| RNA | | 1 | 1 | 1 | 1 | 2 | 2 | 2 | 2 | 4 | 4 | 4 | 4 | 6.6 | 6.6 | 2* | 2* |
| Buffer | | | 2 ul | | 2 ul | | 2 ul | | 2 ul | | 1 ul | | 1 ul | | 1 ul | | 1 ul |
| RNAse T1 | | | 0.5 | | 0.5 | | 0.5 | | 0.5 | | 0.5 | | 0.5 | | 0.5 | | 0.5 |

Note:
all sample stocks are 300 ng/μL, except DNA, which is 1 μg/μL.

RNAse A completely degraded SAM RNA in samples of all concentrations tested, and discriminated DNA from RNA in its sensitivity. Surprisingly though, despite not degrading DNA, RNAse A bound DNA altering its mobility. The DNA binding property confounded interpretation of the results, particularly at low nucleic acid concentration.

Example 3—Feasibility of Using the Ribonuclease RNAse T1

RNase T1 is an endoribonuclease that specifically degrades single-stranded RNA at G residue. The feasibility of an assay that uses RNAse T1 to distinguish SAM RNA from DNA was investigated, using methodology as described above. See Table 2 for experimental set up and FIG. 2 for results.

TABLE 2

Experimental set up for the RNAse Ti mediated assay.

| | Ladder | RNA 1 | DNA 2 | RNA 3 | DNA 4 | RNA 5 | DNA 6 | RNA 7 | DNA 8 | RNA 9 | DNA 10 | RNA 11 | DNA 12 | RNA 13 | DNA 14 | RNA 15 | DNA 16 |
|---|---|---|---|---|---|---|---|---|---|---|---|---|---|---|---|---|---|
| Ladder | 4 ul | | | | | | | | | | | | | | | | |
| RNA | | 1 | 1 | 1 | 1 | 2 | 2 | 2 | 2 | 4 | 4 | 4 | 4 | 6.6 | 6.6 | 2* | 2* |
| Buffer | | | 2 ul | | 2 ul | | 2 ul | | 2 ul | | 1 ul | | 1 ul | | 1 ul | | 1 ul |
| RNAse T1 | | | 0.5 | | 0.5 | | 0.5 | | 0.5 | | 0.5 | | 0.5 | | 0.5 | | 0.5 |
| H2O | 6 ul | 19 | 16.5 | 19 | 16.5 | 18 | 16 | 18 | 16 | 16 | 15 | 16 | 15 | 13 | 12 | 18 | 16 |

Note:
gels are shown with decreasing concentrations of nucleic acids from left to right. Also, all sample stocks are 300 ng/μL, except DNA, which is 1 μg/μL.

RNAse T1 completely degraded SAM RNA in all concentrations tested, and distinguished DNA from RNA in its sensitivity. Additionally, and in contrast to RNAse A (FIG. 1), RNAse T1 did not bind to DNA, not affecting it's mobility on the gel. The results from the assay were sufficiently interpretable to allow RNase T1 to distinguish SAM RNA from DNA. However, it was incapable of differentiating SAM RNA from other contaminating RNA in drug substance and drug product samples. Additionally, the assay does not discriminate between two different SAM RNAs.

Example 4—Feasibility of a RNase H-Based Identity Assay that Discriminates RNA from Other Contaminating RNAs RNAse H is an endoribonuclease that cleaves RNA when it is base paired to single stranded DNA. This property of RNAse H can be utilized to cleave SAM RNA at a specific site by targeting SAM RNA with a short complementary DNA oligo, thereby identifying the SAM RNA in the sample. Cleavage by RNAse H leaves two RNA fragments with sizes corresponding to the site of RNAse H cleavage.

The RNAse H-generated fragments are separated on a denaturing agarose gel and the RNA fragment sizes are assessed to positively identify the SAM RNA in the sample (experimental set up in FIG. 4). Given that single or double stranded DNA are not cleaved by RNAse H, this is a reliable method to distinguish SAM RNA from the template DNA used for synthesizing SAM RNA. Additionally, given that DNA oligos can be designed specifically to target SAM RNAs with inserts of different antigenic regions, this method allows distinguishing different SAM RNAs.

TABLE 4

Experimental set up for the RNAse H mediated assay (FIG. 4).

| | 1 | 2 | 3 | 4 | 5 | 6 | 7 | 8 | 9 |
|---|---|---|---|---|---|---|---|---|---|
| Ladder | 4 | | | | | | | | |
| RNA/DNA | | 3.33 | 3.33 | 3.33 | 3.33 | 3.33 | 1 | 1 | 1 |
| Oligo 1 | | 3.12 ul | | | 3.12 | | | 3.12 | |
| Oligo 2 | | | 3.12 | | | 3.12 ul | | | 3.12 ul |
| Buffer | | 1 ul | 1 ul | 1 ul | 1 ul | 1 ul | 1 ul | 1 ul | 1 ul |
| RNAseH | | | | 1.0 ul | | | 1.0 ul | | 1.0 ul |
| H2O | 6 | 5.67 | 2.55 | 1.55 | 5.67 | 2.55 | 8 | 4.88 | 3.88 |

Note:
all sample stocks are 300 ng/µL, except DNA, which is 1 µg/µL.

TABLE 5

Experimental set up for the RNAse H mediated assay (FIG. 5).

| | 1 | 2 | 3 | 4 | 5 | 6 | 7 | 8 | 9 | 10 | 11 | 12 |
|---|---|---|---|---|---|---|---|---|---|---|---|---|
| Ladder | 4 | | | | | | | | | 4 | | |
| RNA | | 3.33 | 3.33 | 3.33 | 3.33 | 3.33 | 3.33 | 3.33 | 3.33 | | 3.3 | 3.33 |
| SAM Oligo | | | | 3.12 | | | | 3.12 | | | | |
| SAM Rab 1 oligo | | | | | 3.12 | | | | | | | 3.12 |
| SAM Rab 2 oligo | | | | | | | | | 3.12 | | 3.1 | |
| Buffer | | 1 ul | 1 ul | 1 ul | 1 ul | 1 ul | 1 ul | 1 ul | 1 ul | | 1 ul | 1 ul |
| RNAseH | | | 1 | 1 | 1.0 ul | | 1 | 1.0 ul | 1 | | 1 | 1.0 |
| H2O | 6 | 5.67 | 4.67 | 1.55 | 1.55 | 5.67 | 4.67 | 1.55 | 1.55 | 6 | 1.6 | 1.55 |

Note:
all sample stocks are 300 ng/µL.

SEQUENCE LISTINGS

Nucleotide sequence of
SEQ ID NO: 1:
6021 (SAM Oligo): 5'-GCACGGTTCACACTAGATGA-3'

SEQ ID NO: 2:
7811: 5'-GGCACATTGAGGAATTCGTC-3'

SEQ ID NO: 3:
7641: 5'-CCAAGGGCCGAGCTTATCGG-3'

SEQ ID NO: 4:
7581: 5'-GACCAGCAGGGGCACGAACA-3'

SEQ ID NO: 5:
AA095: 5'-GTGTAGATGGGGAACTTGCC-3'

The invention claimed is:

1. A process of manufacturing a vaccine product comprising a subject RNA, the process comprising the steps of:
   (a) manufacturing an RNA from a template DNA and obtaining a sample of the RNA;
   (b) confirming the identity of the RNA in the sample as that of the subject RNA using a method comprising the steps of:
      (A) contacting the sample with a query nucleic acid consisting of a DNA oligonucleotide complementary to a portion of the subject RNA under conditions that the query DNA oligonucleotide specifically hybridizes with the subject RNA vaccine product, when present, to form a hybrid duplex, wherein the formation of the hybrid duplex is carried out at a temperature between 0-10° C.;
      (B) adding an enzyme consisting of RNAse H to the sample under conditions that facilitate specific cleavage of the subject RNA vaccine product when the hybrid duplex is present;
      (C) size fractionating of the sample by denaturing agarose gel electrophoresis and determining the presence of cleaved subject RNA vaccine product by detecting all cleavage products of the subject RNA vaccine product,
      wherein said method can distinguish between a subject RNA vaccine product and a RNA sharing at least 80% sequence homology,
      wherein the identity of the RNA is confirmed as that of the subject RNA where (i) all cleavage products of the subject RNA vaccine product are of predicted size and (ii) contaminating template DNA uncleaved products are not detected;
   and
      (D) utilizing the vaccine product if the identity of the RNA is confirmed.

2. The method of claim 1, wherein the query nucleic acid has a length of 12, or more, nucleotides.

3. The method of claim 1, wherein the molar ratio of the query nucleic acid to subject nucleic acid is between 50:1 and 10000:1, inclusive.

4. The method of claim 3, wherein the molar ratio of the query nucleic acid to subject nucleic acid is about 1000:1.

5. The method of claim 1, wherein the query nucleic acid comprises between 40-60% G-C content, inclusive.

6. The method of claim 5, wherein the query nucleic acid comprises about 50% G-C content.

7. The method of claim 1, wherein the formation of the hybrid duplex is carried out for a period of time between 1-60 minutes.

8. The method of claim 1, wherein the specific cleavage of the subject nucleic acid is carried out at a temperature of between 0-50° C., inclusive.

9. The method of claim 8, wherein the specific cleavage of the subject nucleic acid is carried out at a temperature of about 37° C.

10. The method of claim 1, wherein the products are not subject to a sequencing reaction.

11. The method of claim 1, wherein the subject RNA encodes a polypeptide of interest.

* * * * *

SEQUENCE LISTING

<160> NUMBER OF SEQ IDS NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic alpha viral vector sequence

<400> SEQUENCE: 1
gcacggttca cactagatga          20

<210> SEQ ID NO 2
<211> LENGTH: 20
<212> TYPE: DNA
<213> ORGANISM: Artificial Sequence
<220> FEATURE:
<223> OTHER INFORMATION: Synthetic alpha viral vector sequence

<400> SEQUENCE: 2
ggcacattga ggaattcgtc          20

```
<210> SEQ ID NO 3
<211> LENGTH: 20
<212> TYPE: DNA
<213> ORGANISM: Artificial Sequence
<220> FEATURE:
<223> OTHER INFORMATION: Synthetic alpha viral vector sequence

<400> SEQUENCE: 3
ccaagggccg agcttatcgg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic alpha viral vector sequence

<400> SEQUENCE: 4
gaccagcagg ggcacgaaca                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic alpha viral vector sequence

<400> SEQUENCE: 5
gtgtagatgg ggaacttgcc                                              20
```